United States Patent [19]

Shibanuma et al.

[11] Patent Number: 4,845,211

[45] Date of Patent: Jul. 4, 1989

[54] AMINO-3-SUBSTITUTED-METHYL-3-CEPHEM-4-CARBOXYLIC ACID AND LOWER ALKYLSILYL DERIVATIVES THEREOF

[75] Inventors: Tadao Shibanuma; Kohji Nakano; Noriaki Nagano; Yukiyasu Murakami, all of Saitama; Ryuichiro Hara, Tokyo; Akio Koda, Tokyo; Atsuki Yamazaki, Tokyo, all of Japan

[73] Assignee: Yamanouchi Pharmaceutical Co., Ltd., Tokyo, Japan

[21] Appl. No.: 46,661

[22] Filed: May 4, 1987

Related U.S. Application Data

[62] Division of Ser. No. 699,584, Feb. 8, 1985, Pat. No. 4,699,980.

[30] Foreign Application Priority Data

Feb. 10, 1984 [JP] Japan .................................. 59-24110

[51] Int. Cl.$^4$ .................. C07D 501/38; A61K 31/545
[52] U.S. Cl. ..................... 540/224; 540/225; 540/222
[58] Field of Search ............... 540/227, 224, 222, 225, 540/226

[56] References Cited

U.S. PATENT DOCUMENTS

| | | | |
|---|---|---|---|
| 4,407,798 | 10/1983 | Kamiya et al. | 540/225 |
| 4,540,779 | 9/1985 | Conrad et al. | 540/225 |
| 4,609,653 | 9/1986 | Dürckheimer | 540/225 |
| 4,665,168 | 5/1987 | Chou et al. | 540/224 |
| 4,703,118 | 10/1987 | Lord et al. | 540/225 |

FOREIGN PATENT DOCUMENTS

0154417  9/1985  European Pat. Off. .

*Primary Examiner*—Nicholas S. Rizzo
*Attorney, Agent, or Firm*—Burgess, Ryan and Wayne

[57] ABSTRACT

Various 7-amino-3-substituted-methyl-3-cephem-4-carboxylic acids and lower alkylsily derivatives such as 7-amino-3-(2,3-cyclopenteno-1-pyridiniomethyl)-3-cephem-4 -carboxylic acid iodide and trimethylsilyl 7-trimethylsilylamino-3 -(5,6,7,8-tetrahydro-2-isoquinoliniomethyl)-3-cephem-4 -carboxylate iodide are valuable intermediates in the preparation of new and novel antibacterial agents. A new process for the preparation of these acids and the derivatives has been devised.

8 Claims, No Drawings

AMINO-3-SUBSTITUTED-METHYL-3-CEPHEM-4-CARBOXYLIC ACID AND LOWER ALKYLSILYL DERIVATIVES THEREOF

This is a division of application Ser. No. 699,584, filed Feb. 8, 1985 now U.S. Pat. No. 4,699,980.

BACKGROUND OF THE INVENTION

1. Field of the Invention

This invention relates to chemical compounds useful as chemical intermediates in the preparation of valuable antibiotic substances.

2. Description of the Prior Art

There exists a need to provide alternate and more efficient methods of producing key intermediates necessary for the preparation of new and valuable antibacterial agents. The new intermediate compounds and process for their preparation were heretofor unknown.

DETAILED EXPLANATION OF THE INVENTION

Compounds having the formula (I₁)

wherein —⊕A represents (wherein $R^2$ is a hydrogen atom or an amino group, and n is an integer of 1 to 2); $Y^\ominus$ represents an anion; and $R^1$ represents a lower alkyl group; are prepared by a process which comprises reacting 7-amino-3-halogenomethyl-3-cephem-4-carboxylic acid of the formula (II)

(wherein X is a halogen atom) with (tri-loweralkylsilyl)-trifluoroacetamide of the formula $$F_3C-\underset{|}{\overset{O-Si(R^1)_3}{C}}=N-Si(R^1)_3 \quad \text{or} \quad F_3C-\underset{|}{\overset{O}{\overset{\|}{C}}}-\underset{|}{\overset{CH_3}{N}}-Si(R^1)_3$$
$$(III_1) \qquad\qquad (III_2)$$

(wherein $R^1$ is as defined above) and a pyridine compound of the formula (IV)

(wherein $R^2$ and n are as defined above).

If necessary, by releasing the protective groups [namely, $(R^1)_3Si$-], 7-amino-3-substituted-methyl-3-cephem-4-carboxylic acid (or carboxylate) of the formula (I₂)

(I₂)

are prepared.

Schematically, the reaction sequence may be illustrated as below.

(II)

(wherein X is a halogen atom)

$$F_3C-\underset{|}{\overset{O-Si(R^1)_3}{C}}=N-Si(R^1)_3 \quad \text{or} \quad F_3C-\underset{|}{\overset{O}{\overset{\|}{C}}}-\underset{|}{\overset{CH_3}{N}}-Si(R^1)_3$$
$$(III_1) \qquad\qquad (III_2)$$

(wherein $R^1$ is as defined above)

(wherein $R^2$ and n are as defined above)

(I₁)

wherein —⊕A represents

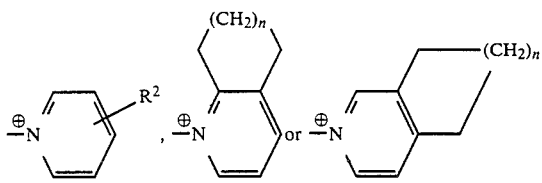

(wherein $R^2$ is a hydrogen atom or an amino group, and n is an integer of 1 to 2); $Y^\ominus$ represents an anion; and $R^1$ represents a lower alkyl group;

↓ removal of tri-loweralkylsilyl groups

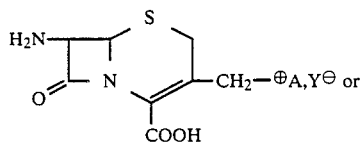  (I$_2$)

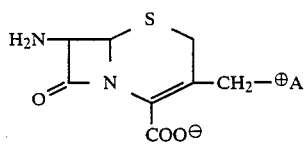

This invention relates mostly to novel compounds and the process therefor. More particularly, this invention relates to novel compounds which are useful as intermediates in the preparation of therapeutically active cephalosporins, and to the processes for preparing such compounds.

It is an object of the present invention to provide chemical intermediates which can be easily converted to cephalosprins and other therapeutically useful substances. It is another object of the present invention to provide a novel process for the preparation of these compounds.

The main objective of the present invention is the synthesis of valuable key intermediates in the ultimate synthesis of particular final compounds, i.e. cephalosporins having a substituted pyridinio group at the 3-position.

The primary objective of the present invention is to prepare intermediates that are readily converted into compounds disclosed in the inventor's co-pending patent applications such as U.S. patent application Ser. No. 656,162 and European Patent Application No. 84 306967.5.

The present invention is explained in more detail below.

Examples of the pyridine compounds used for the reaction of the present invention are pyridine, 4-aminopyridine, 3-aminopyridine, 2-aminopyridine, 2,3-cyclopentenopyridine, 5,6,7,8-tetrahydroquinoline, 3,4-cyclopentenopyridine, 5,6,7,8-tetrahydroisoquinoline, etc.

Examples of the group represented by $-\oplus A$ are pyridinium, aminopyridinium

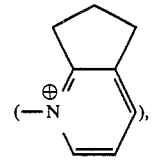

2,3-cyclopenteno-1-pyridinium

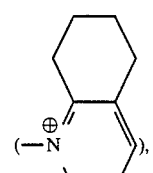

5,6,7,8-tetrahydro-1-quinolinium

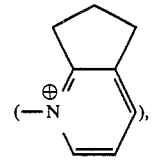

3,4-cyclopenteno-1-pyridinium

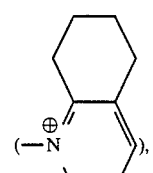

5,6,7,8-tetrahydro-2-isoquinolinium

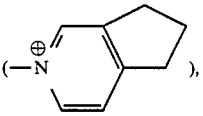

etc.

Examples of the anion of the formula $Y^\ominus$ are inorganic anions such as a halogen anion ($Cl^\ominus$, $I^\ominus$, etc.), and a sulfonate anion ($HSO_4^\ominus$, $SO_4^{\ominus\ominus}$, etc.); and organic anions such as a benzenesulfonate anion ($C_6H_5SO_3^\ominus$), an acetate anion ($CH_3COO^\ominus$), a fumarate anion (HOOC—CH=CH—COO$^\ominus$), a citrate anion

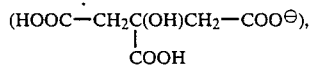

etc.

Examples of "Halogen" in the foregoing definition are chlorine, bromine, iodine, and fluorine.

Examples of "lower alkyl" are methyl, ethyl, propyl, butyl, iso-butyl, etc. Thus, typical lower alkyl is straight or branched carbon chain alkyl having 1 to 5 carbon atoms.

The compounds (prepared by the process of this invention) of the formula (I$_1$) are novel compounds. And, the compounds (prepared by the process of this invention) of the formula (I$_2$) except 7-amino-3-pyridiniomethyl-3-cephem-4-carboxylate (namely,

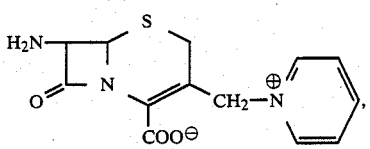

are also novel compounds.

A known process for producing the above known compound (namely, 7-amino-3-pyridiniomethyl-3-cephem-4-carboxylate) are disclosed in unexamined Japanese patent application laid-open under the laying-open No. Sho. 56-12397, and the known process comprises hydrolysing cafaloridin which is known as a valuable antibacterial compound. However, this known process is not economical, and is not suitable for the practical production of the compound.

The process of the present invention is entirely different from the known process, and has a characteristic in that 7-amino-3-halgenomethyl cephalosporanic acid (II), which is easily available, is used as starting material. Further, the loweralkylsilyl compounds of this invention are easily soluble in organic solvents, and side reactions such as rearrangement of double bond at the 2-position of the cephalorsporin nucleus ($\Delta^3 \to \Delta^2$ rearrangement) do not occur in the process of this invention even when reacting nucleophilic reagent such as pyridine compounds. Thus, the process of this invention exhibits high yield and high purity.

So, the process of this invention is excellent in case of industrial manufacturing of cephalosporin compounds.

In the process of this invention, 7-amino-3-halogenomethyl-3-cephem-4-carboxylic acid (II) or a salt thereof is reacted with (tri-loweralkylsilyl)trifluoroacetamide (III$_1$ or III$_2$) and pyridine compound (IV) in an organic solvent which is inert for the reaction.

As (tri-loweralkylsilyl)trifluoroacetamide, is used O,N-bis(tri-loweralkylsilyl)trifluoroacetamide (III$_1$) or N-methyl-N-tri-loweralkylsilyltrifluoroacetamide (III$_2$). Preferable examples of the compounds (III$_1$) and (III$_2$) are O,N-bis(trimethylsilyl)trifluoroacetamide

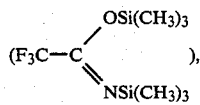

N-methyl-N-trimethylsilyltrifluoroacetamide

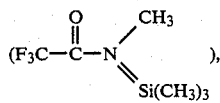

When reacting 7-amino-3-halogenomethyl-3-cephem-4-carboxylic acid with (tri-loweralkylsilyl)trifluoroacetamide (III$_1$ or III$_2$) and pyridine compound (IV), it is preferred that 7-amino-3-halogenomethyl-3-cephem-4-carboxylic acid is, first, reacted with (tri-loweralkylsilyl)trifluoroacetamide (III$_1$ or III$_2$), and then with pyridine compound (IV) (that is, 2 step reaction). However, (Tri-loweralkylsilyl)trifluoroacetamide (III$_1$ or III$_2$) and pyridine compound (IV) can be reacted simultaneously with 7-amino-3-halogenomethyl-3-cephem-4-carboxylic acid.

The reaction proceeds easily at room temperature. When performing the reaction in 2 steps, the 1st step may be performed at room temperature and the 2nd step may be performed under heating or cooling at a temperature from $-20°$ C. to $40°$ C. Examples of the inert organic solvent usually used are dichlromethane, acetone, acetonitrile, tetrahydrofuran, and chloroform.

In the process of invention, tri-loweralkylsilyl compounds (I$_1$) are produced. The compounds (I$_1$) can be used, as it is, as starting materials for various cephalosporin compounds which may be valuable antibacterial agents. That is, the compounds (I$_1$) can be subjected directly to the next reaction for producing the valuable cephalosporin compounds. However, the compounds (I$_2$) obtained after releasing the tri-loweralkylsilyl groups (protective groups) can be used as starting materials for producing the valuable cephalosporin compounds, if necessary.

The removal of the protective groups for the reaction product is easily performed, by treatment with water or alcohol-solvent. Examples of alcohol are mono-OH alcohol (such as methanol, ethanol, propanol) and di-OH alcohol (such as 1,2-ethanediol, 1,3-propanediol, 1,3-butanediol). It is preferred to use 1,3-butanediol, in view of the ease of separation and purification of the formed compounds.

The manufacturing process and the process of this invention will be further explained by the following Reference-Examples and -Explanation and Examples. Reference explanation and Reference Examples show the manufacturing process for producing 7-substituted aminocephalosporin compounds by introducing a substituent at 7-amino position of the cephalosporin nucleus of the compounds of this invention.

REFERENCE EXPLANATION

Cephalosporin derivatives claimed in the inventors' co-pending applications (U.S. patent application Ser. No. 656,162 and European Patent Application No. 84 306967.5) are prepared from the compounds of this invention by amidation (acylation) at the 7-amino group position in the compounds of this invention by using suitable acylating agents. This amidation reaction is explained below.

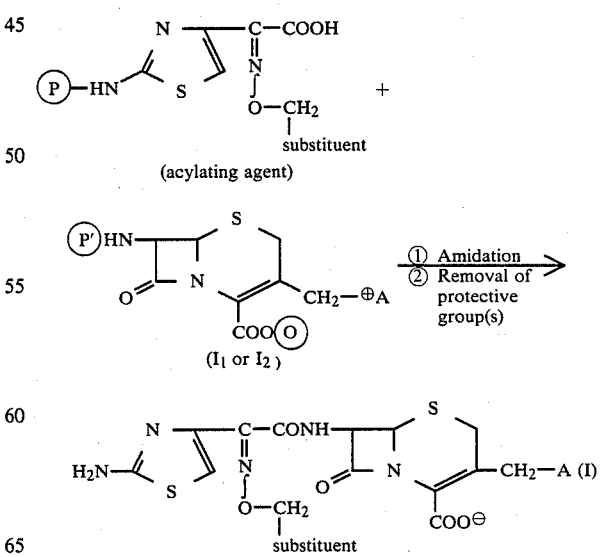

In the above formulae, Ⓟ is a hydrogen atom or a protective group for an amino group, Ⓟ' is a hydrogen atom or a tri-loweralkylsilyl group; and Q is a hydrogen atom or a tri-loweralkylsilyl group; —A⊕ is as defined above.

Compounds I (valuable cephalosporin compounds) can thus be produced by reacting substituted oxyiminothiazolylacetic acid derivative or reactive derivative thereof with 7-amino-3-cephem derivative (I₁ and I₂) and then, if necessary, releasing any protective group(s).

In this case the protective group for an amino group may be one usually used in the field of peptide chemistry and practical examples are acyl groups such as a formyl group, an acetyl group, a propionyl group, a tert-butoxycarbonyl group, a methoxyacetyl group, a methoxypropionyl group, a benzyloxycarbonyl group, a p-nitrobenzyloxycarbonyl group; tri-loweralkylsilyl groups such as a trimethylsilyl group; and aralkyl groups such as a benzyl group, a benzhydryl group (diphenylmethyl group), a trityl group.

The reaction is usually performed in a solvent under cooling at room temperature or below. Any solvents which do not take part in the reaction can be used. Examples of the solvent usually used are organic solvents such as dioxane, tetrahydrofuran, ether, acetone, ethyl methyl ketone, chloroform, dichloromethane, dichloroethane, methanol, ethanol, acetonitrile, ethyl acetate, ethyl formate, dimethylformamide, dimethyl sulfoxide; these solvents may be used alone or in appropriate combination.

The acylating agent may be a free carboxylic acid or a reactive derivative thereof. Suitable examples of the compound are mixed acid anhydrides, acid anhydrides, acid halides, active esters, active amides, acid azides. When using the compound in the form of a free carboxylic acid, it is preferred to use a condensing agent such as N,N'-dicyclo-hexylcarbodiimide or N,N'-diethylcarbodiimide.

According to the kind of reactive derivative of carboxylic acid used, it may be preferred for smooth reaction to operate in the presence of a base. Examples of such a base are inorganic bases such as sodium hydrogencarbonate, potassium hydrogencarbonate, sodium carbonate, potassium carbonate; and organic bases such as trimethylamine, triethylamine, dimethylaniline, pyridine.

EXAMPLE 1 pyridine was added thereto. After stirring the solution for 4 hours at the same temperature, 1.6 ml of 1,3-butanediol was added thereto. Precipitates thus formed were collected by filtration, washed with 30 ml of dichloromethane, and dried to provide 730 mg of 7-amino-3-(1-pyridiniomethyl)-3-cephem-4-carboxylic acid iodide.

NMR(DMSO-d₆) δ 5.09, 5.19 (each 1H, each d,

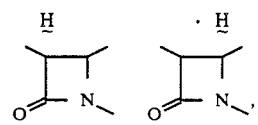

5.58 (2H, s,

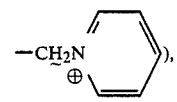

8.24 (2H, t,

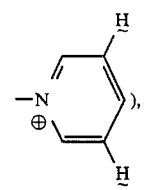

8.70 (1H, t,

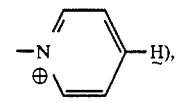

9.10 (2H, d,

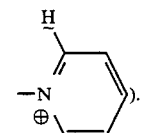

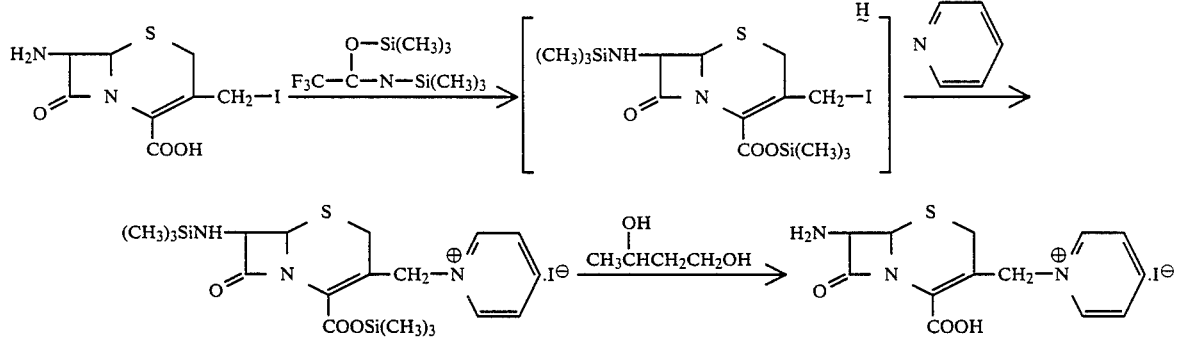

In 10 ml of dichloromethane was suspended 680 mg of 7-amino-3-iodomethyl-3-cephem-4-carboxylic acid and after adding thereto 1.2 ml of O,N-bis(trimethylsilyl)trifluoroacetamide, the mixture was stirred for 30 minutes at room temperature to form a clear solution. The solution was cooled to 5° to 6° C., and 316 mg of Using the compound of Example 1 as a starting material, the following compound was obtained.

REFERENCE EXAMPLE 1

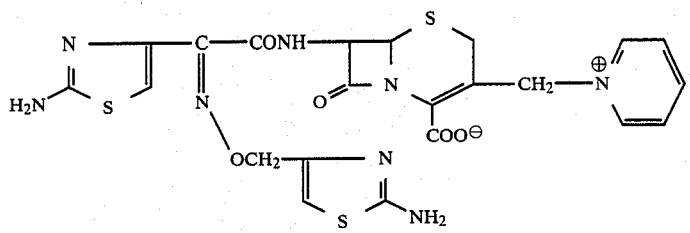

(i) In 10 ml of dichloromethane was suspended 419 mg of 7-amino-3-(1-pyridiniomethyl)-3-cephem-4-carboxylic acid iodide and after adding thereto 0.9 ml of O,N-bis(trimethylsilyl)trifluoroacetamide, the mixture was stirred for 30 minutes to form a clear solution. The solution was cooled to $-40°$ C., and 0.5 ml of pyridine was added thereto. (The solution thus formed is hereafter referred to as "Solution A".)

In 10 ml of dichloromethane was suspended 783 mg of (Z)-α-(2-tritylamino-4-thiazolyl)-α-[(2-tritylamino-4-thiazolyl)methoxyimino]acetic acid and after cooling the suspension to 3° to 4° C., 208 mg of phosphorus pentachloride was added thereto, and the mixture was stirred for 15 minutes at 3°-4° C. (The solution thus formed is hereafter referred to as "Solution B".)

Solution B was added dropwise to solution A and the temperature of the reaction mixture was elevated to $-10°$ C. over 15 minutes. After adding to the reaction mixture 1 ml of water, 1 ml of tetrahydrofuran and 3 ml of 1N-hydrochloric acid, the mixture was stirred for 10 minutes at $-10°$-$0°$ C. The reaction mixture was distilled under reduced pressure to remove dichloromethane and tetrahydrofuran and after adding to the residue obtained 50 ml of water, precipitates (powder) thus formed were collected by filtration, washed with water, and dried to provide 0.91 g of a crude product (a compound having protective groups).

(ii) After adding to the crude product obtained as above 20 ml of trifluoroacetic acid and 6 ml of water under ice-cooling, the mixture was stirred for 1 hour at room temperature. Insoluble materials were removed by filtration, and the filtrate was concentrated under reduced pressure. To the residue was added 20 ml of ether, and the powder thus formed was collected by filtration to provide 0.45 g of a crude product. The crude product was suspended in 50 ml of water and after adding 2 ml of 1N-hydrochloric acid, the formed solution was subjected to column chromatography on Diaioh HP-20 and the product was eluted first with water and then with mixtures of water-methanol of successively changing mixing ratio. The fractions containing the desired product were concentrated, and lyophilized to provide 80 mg of (Z)-7-{α-(2-amino-4-thiazolyl)-α-[(2-amino-4-thiazolyl)methoxyimino]acetamido}-3-(1-pyridiniomethyl)3-cephem-4-carboxylate.

NMR(DMSO-$d_6$) δ(ppm): 4.88(2H,

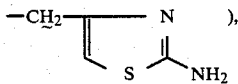

), 5.08(1H,

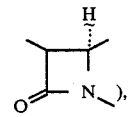

), 5.72(1H,

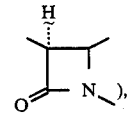

), 6.40, 6.68 (each 1H,

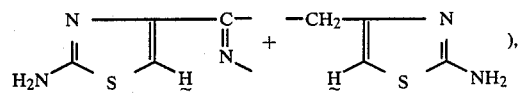

), 8.13(2H,

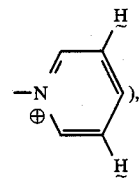

), 8.57(1H,

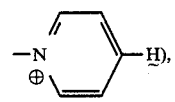

), 9.39(2H,

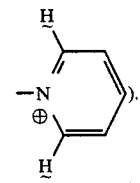

),

EXAMPLE 2

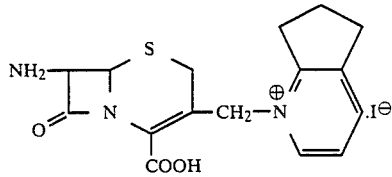

In 50 ml of dichloromethane was suspended 1.7 g of 7-amino-3-iodomethyl-3-cephem-4-carboxylic acid and after adding thereto 2.8 ml of O,N-bis(trimethylsilyl)trifluoroacetamido, the mixture was stirred for 30 minutes at room temperature to form a clear solution. After adding thereto 654 mg of 2,3-cyclopentenopyridine, the solution was stirred for 4 hours at room temperature to provide trimethylsilyl 7-trimethylsilylamino-3-(2,3-cyclopenteno-1-pyridiniomethyl)-3-cephem-4-carboxylate iodide. After adding thereto first 4 ml of 1,3-butanediol, and then adding 150 ml of ether, precipitates thus formed were collected by filtration, washed with 50 ml of ether, and dried to provide 1.8 g of 7-amino-3-(2,3-cyclopenteno-1-pyridiniomethyl)-3-cephem-4-carboxylic acid iodide.

NMR(DMSO-$d_6$) δ (ppm) 1.90–2.40 (2H, m,

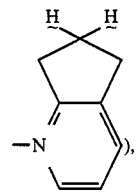

2.8–3.9 (6H, m,

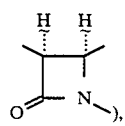

5.10, 5.21 (each 1H, each d,

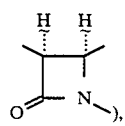

5.49 (2H, s, 7.86 (1H, t,

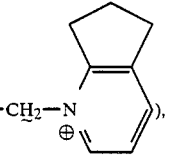

8.34 (1H, d,

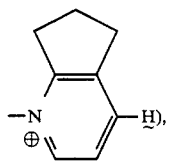

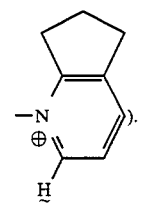

8.64 (1H, d,

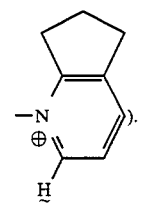

Using, as a starting material, trimethylsilyl 7-trimethylsilylamino-3-(2,3-cyclopenteno-1-pyridiniomethyl)-3-cephem-4-carboxylate iodide obtained in the reaction course of Example 2, the following compound was obtained.

REFERENCE EXAMPLE 2

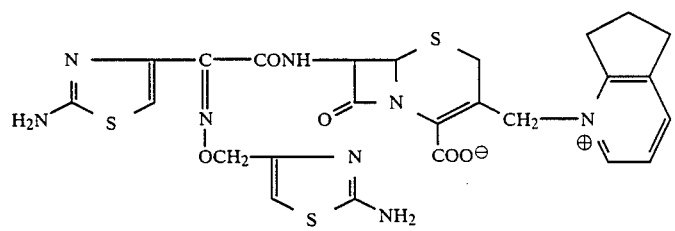

In 25 ml of dichloromethane was suspended 3.92 g of (Z)-α-(2-tritylamino-4-thiazolyl)-α-[(2-tritylamino-4-thiazolyl)methoxyimino]acetic acid and after cooling the suspension to 3° to 4° C. and then adding thereto 1.04 g of phosphorus pentachloride, the mixture was stirred for 15 minutes at 3°–4° C. (The solution thus formed is hereafter referred to as "Solution A".)

A solution containing trimethylsilyl 7-trimethylsilylamino-3-(2,3-cyclopenteno-1-pyridiniomethyl)-3-cephem-4-carboxylate iodide obtained in the reaction course of Example 2 was cooled to −50° C., and 2.2 ml of pyridine was added thereto. (The solution thus formed is hereafter referred to as "Solution B".)

Solution A was added dropwise to solution B, and the temperature of the reaction mixture was increased to −15° C. over 15 minutes. After adding thereto 5 ml of water, 10 ml of tetrahydrofuran, and 10 ml of 1N-hydrochloric acid, the resultant solution was stirred for 10 minutes under ice-cooling. The reaction mixture was distilled under reduced pressure to remove dichloromethane and tetrahydrofuran and after adding to the residue obtained 200 ml of water, precipitates thus formed were collected by filtration. The precipitates obtained was washed with water, and dried to provide 5.5 g of a crude product (a compound having protective groups). After adding to the crude product 60 ml of trifluoroacetic acid and 12 ml of water under ice-cooling, the mixture was stirred for 1 hour at room temperature. Insoluble materials were removed by filtration, and the filtrate was concentrated under reduced pressure. To the residue was added 150 ml of ether to form a powder, and the powder was collected by filtration to provide 2.7 g of a crude product. The crude product was suspended in 200 ml of water and after adding thereto 4 ml of 1N-hydrochloric acid, the formed solution was subjected to column chromatography on Diaion HP-20 and the product was eluted first with water and then mixtures of water and methanol of successively changing mixing ratio (water:methanol from 10:1 to 10:6). The fractions containing the desired product were concentrated, and lyophilized to provide 275 mg of (Z)-7-{α-(2-amino-4-thiazolyl)-α-[(2-amino-4-thiazolyl)methoxyimino]acetamido}-3-(2,3-cyclopenteno-1-pyridinyl)-3-cephem-4-carboxylate.

NMR(DMSO-d$_6$) δ 4.89 (2H,

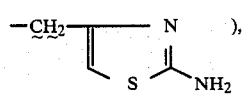

5.06 (1H,

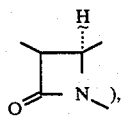

5.70 (1H,

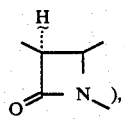

6.44, 6.73 (each 1H,

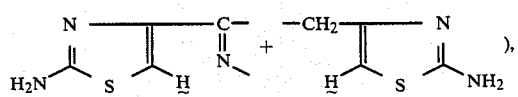

7.83 (1H, 8.63 (1H,

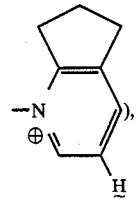

9.19 (1H,

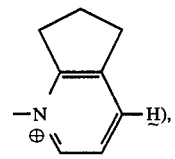

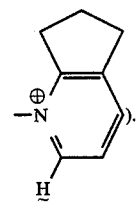

EXAMPLE 3

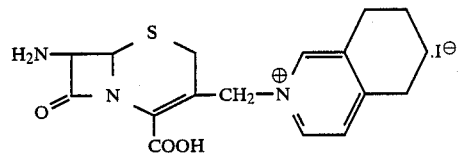

In 50 ml of dichloromethane was suspended 1.7 g of 7-amino-3-iodomethyl-3-cephem-4-carboxylic acid and after adding thereto 2.8 ml of O,N-bis(trimethylsilyl)trifluoroacetamide, the mixture was stirred for 30 minutes at room temperature to form a clear solution. After adding thereto 665 mg of 5,6,7,8-tetrahydroisoquinoline, the solution was stirred for 4 hours at room temperature to provide trimethylsilyl 7-trimethylsilylamino-3-(5,6,7,8-tetrahydro-2-isoquinoliniomethyl)-3-cephem-4-carboxylate iodide. After adding thereto first 4 ml of 1,3-butanediol, and then adding 150 ml of ether, precipitates thus formed were collected by filtration, washed with 50 ml of ether, and dried to provide 2 g of 7-amino-3-(5,6,7,8-tetrahydro-2-isoquinoliniomethyl)-3-cephem-4-carboxylic acid iodide.

NMR(DMSO-d$_6$) δ: ppm 1.60–1.96 (4H, b, 2.60–3.12 (4H, b, 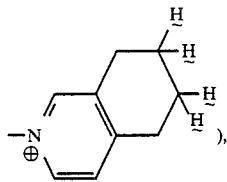

4.98–5.08 (each 1H, each d, 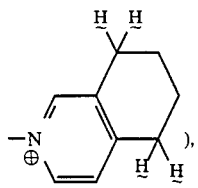

5.40 (2H, s, 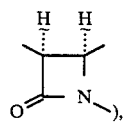

7.82 (1H, d, 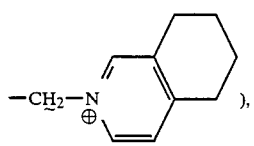

8.60 (1H, d, 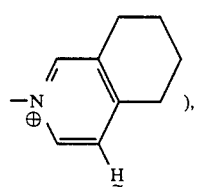

8.72 (1H, s, 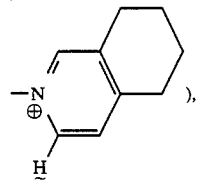

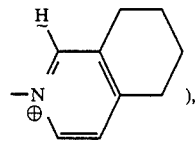),

Using, as a starting material, trimethylsilyl 7-trimethylsilylamino-3-(5,6,7,8-tetrahydro-2-isoquinoliniomethyl)-3-cephem-4-carboxylate iodide obtained in the course of the reaction of Example 3, the following compound was produced.

EXAMPLE 3

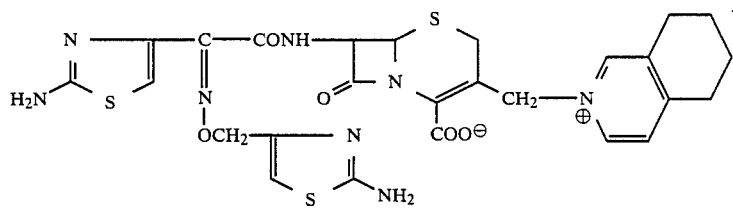

In 25 ml of dichloromethane was suspended 3.92 g of (Z)-α-(2-tritylamino-4-thiazolyl)-α-[(2-tritylamino-4-thiazolyl)methoxyimino]acetic acid and after cooling the suspension to 3° to 4° C. and then adding thereto 1.04 g of phosphorus pentachloride, the mixture was stirred for 15 minutes at 3°–4° C. (The solution thus formed is hereafter referred to as "Solution A".)

A solution containing trimethylsilyl 7-trimethylsilylamino-3-(5,6,7,8-tetrahydro-2-isoquinoliniomethyl)-3-cephem-4-carboxylate iodide in the reaction course of Example 3 was cooled to −50° C., and 2.2 ml of pyridine was added thereto. (The solution thus foremd is hereafter referred to as "Solution B".)

Solution A was added dropwise to solution B, and the temperature of the reaction mixture was increased to −15° C. over 15 minutes. After adding thereto 5 ml of water, 15 ml of 1N-hydrochloric acid, and 10 ml of tetrahydrofuran, the resultant solution was stirred for 10 minutes under ice-cooling. The reaction mixture was distilled under reduced pressure to remove dichloromethane and tetrahydrofuran and after adding to the residue obtained 200 ml of water, precipitates thus formed were collected by filtration to provide 10 g of a crude product containing water (a compound having protective groups). After adding to the curde product 70 ml of trifluoroacetic acid and 14 ml of water under ice-cooling, the mixture was stirred for 1 hour at room temperature. Insoluble materials were removed by filtration, and the filtrate was concentrated under reduced pressure. To the residue was added 200 ml of ether to form a powder, and the powder was collected by filtration to provide 4 g of a crude product. The crude product was suspended in 300 ml of water and after adding 6 ml of 1N-hydrochloric acid, the formed solution was subjected to column chromatography on Diaion HP-20 and the product was eluted first with water and then mixtures of water and methanol of successively changing mixing ratio (water:methanol from 10:1 to 10:7). The fractions containing the desried product were concentrated, and lyophilized to provide 393 mg of (Z)-7-{α-(2-amino-4-thiazolyl)-α-](2-amino-4-thiazolyl)methoxyimino]acetamido}-3-(5,6,7,8-tetrahydro-2-isoquinoliniomethyl)-3-cehem-4-carboxylate.

NMR(DMSO-d$_6$) 1.55–2.00 (4H,

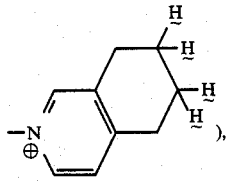), 2.60–3.20 (4H,

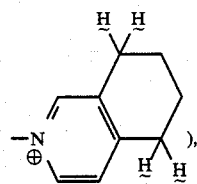), 4.88 (2H,

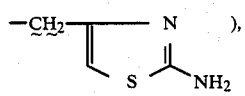), 5.07 (1H,

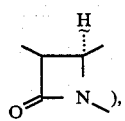), 5.68 (1H,

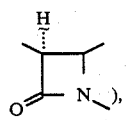), 6.43, 6.73 (each 1H,

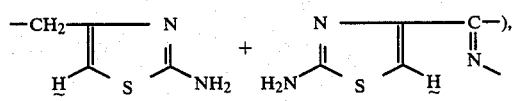), 7.84 (1H, 9.05 (1H,

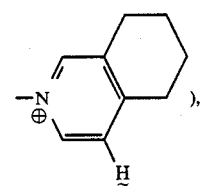), 9.09 (1H,

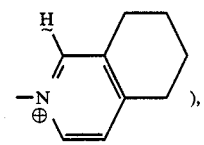),

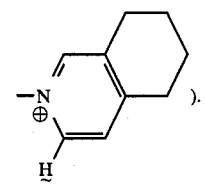).

We claim:
1. A compound of the formula

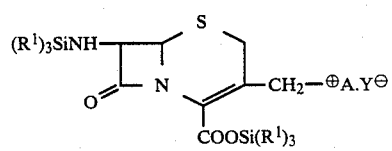 (I₁)

wherein —⊕A represents

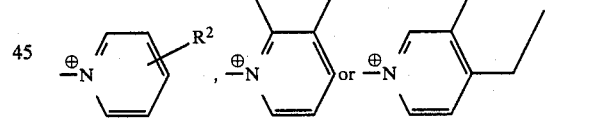

(wherein R² is an amino group, and n is an integer of 1 to 2); Y⊖ represents an organic or inorganic anion; and R¹ represents a lower alkyl group.

2. A compound as claimed in claim 1 wherein R¹ is a methyl group.

3. A compound as claimed in claim 1 wherein an anion is an inorganic anion.

4. A compound as claimed in claim 3 wherein an inorganic anion is an iodine anion.

5. A compound as claimed in claim 1 wherein n is 1.

6. A compound as claimed in claim 1 wherein n is 2.

7. A compound as claimed in claim 1 R² is an amino group.

8. A compound as claimed in claim 1 an anion is a halogen anion.

* * * * *